(12) United States Patent
Bartl et al.

(10) Patent No.: US 7,977,480 B2
(45) Date of Patent: Jul. 12, 2011

(54) SYNTHESIS OF PALIPERIDONE

(75) Inventors: Jiri Bartl, Strelice (CZ); Jozef Krajcovic, Brno (CZ); Petr Benovsky, Brno (CZ)

(73) Assignee: Synthon BV, Nijmegen (NL)

( * ) Notice: Subject to any disclaimer, the term of this patent is extended or adjusted under 35 U.S.C. 154(b) by 302 days.

(21) Appl. No.: 12/331,952

(22) Filed: Dec. 10, 2008

(65) Prior Publication Data

US 2009/0156810 A1    Jun. 18, 2009

Related U.S. Application Data

(60) Provisional application No. 61/012,546, filed on Dec. 10, 2007.

(51) Int. Cl.
*C07D 401/00* (2006.01)
*C07D 403/00* (2006.01)
*C07D 413/00* (2006.01)

(52) U.S. Cl. ..................................... 544/284
(58) Field of Classification Search ........... 544/284
See application file for complete search history.

(56) References Cited

U.S. PATENT DOCUMENTS

| 5,158,952 A | 10/1992 | Janssen et al. |
| 5,688,799 A | 11/1997 | Vandenberk et al. |
| 2009/0036470 A1 | 2/2009 | Bartl et al. |

FOREIGN PATENT DOCUMENTS

| EP | 196132 | 8/1992 |
| EP | 368388 | 5/1995 |
| WO | WO 95/14691 | * 6/1995 |
| WO | WO 2007/026377 | 3/2007 |

OTHER PUBLICATIONS

A. Horvath et al., "Nitrogen Bridgehead Compounds. Part 30. Vilsmeier-Haack Formylation of 6, 7, 8, 9 Tetrahydro-4H-pyrido [1,2-a] pyrimidin-4-ones" (J. Chem. Soc. Perkin Trans. 1, (1983) pp. 369-377.

\* cited by examiner

*Primary Examiner* — James O Wilson
*Assistant Examiner* — Erich A Leeser
(74) *Attorney, Agent, or Firm* — Muncy, Geissler, Olds & Lowe, PLLC

(57) ABSTRACT

A 9-hydroxy or 9-acyloxy group can be added to a pyridopyrimidinone ring structure by a process comprising acylating a compound of formula (5) under Vilsmeier-Haack or Friedel-Crafts conditions to form a compound (6); and transforming with a peroxo-compound to obtain the compound (1).

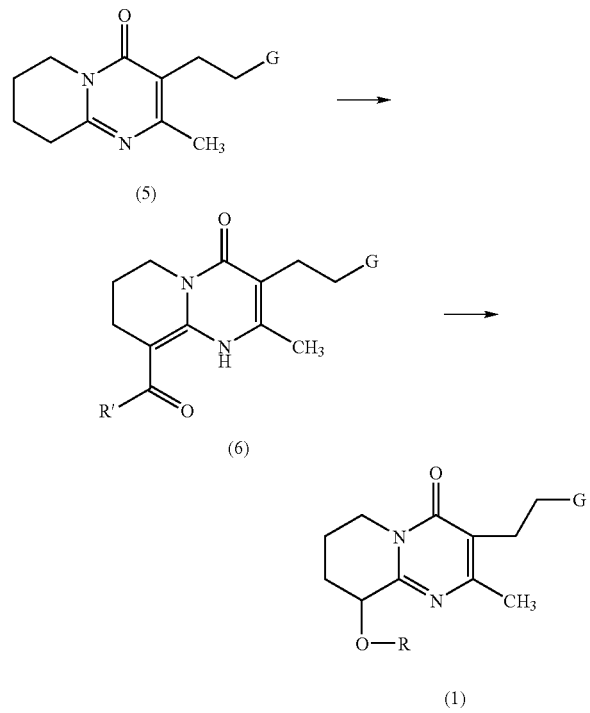

R represents hydrogen or a C1-C20 acyl group. The process is useful in the synthesis of paliperidone and derivatives.

19 Claims, No Drawings

SYNTHESIS OF PALIPERIDONE

This application claims the benefit of priority under 35 U.S.C. §119(e) from U.S. Provisional Application Ser. No. 61/012,546, filed Dec. 10, 2007, the entire contents of which are incorporated herein by reference.

BACKGROUND OF THE INVENTION

Paliperidone, or 9-hydroxyrisperidone (chemically: (±)-3-(2-(4-(6-fluoro-1,2-benzisoxazol-3-yl)-1-piperidinyl)ethyl)-6,7,8,9-tetrahydro-9-hydroxy-2-methyl-4H-pyrido[1,2-a]pyrimidin-4-one) of the formula (I):

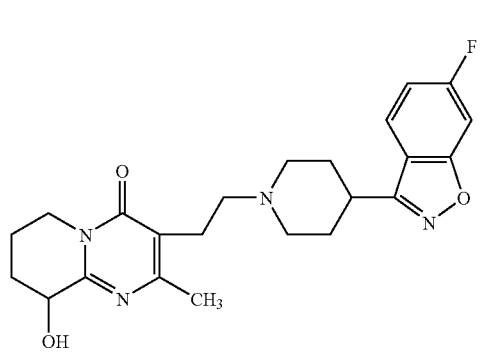

(I)

is a major human metabolite of the known antipsychotic drug risperidone. It is marketed in tablets for oral administration under the brand name INVEGA™ (Janssen, L. P.) for treatment of schizophrenia. Paliperidone has one centre of optical activity (the carbon in the 9-position); both enantiomers are known but the marketed compound is a racemate.

Paliperidone (including enantiomeric forms thereof) has been disclosed in EP 368388 (U.S. Pat. No. 5,158,952). The same document discloses also esters of paliperidone with carboxylic acids having the formula (II) ($R'=C_{1-19}$ alkyl).

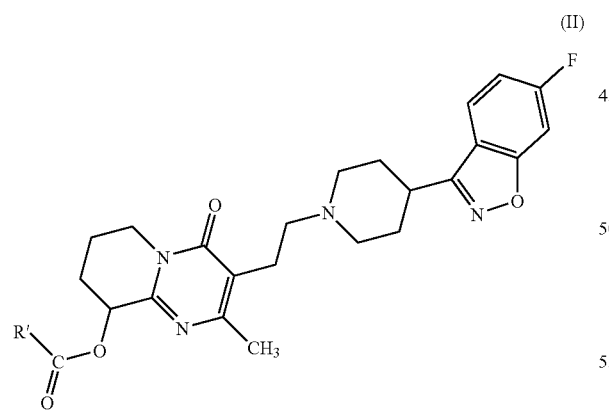

(II)

A preferred ester compound (II) is paliperidone palmitate, which is currently under development for use in injectable compositions with prolonged action.

Various processes for making compounds of formula (I) and (II) have been generally disclosed in the EP 368388. One process is based on an alkylation of a 3-piperidinyl 1,2-benzisoxazole of the formula (2) with the compound of formula (1.1), wherein R is hydrogen or C1-C20 acyl group and A represents an appropriate leaving group such as, for example, halo, e.g., chloro, bromo or iodo; sulfonyloxy, e.g., methanesulfonyloxy, trifluoromethanesulfonyloxy, benzenesulfonyloxy, 4-methylbenzenesulfonyloxy and the like leaving groups.

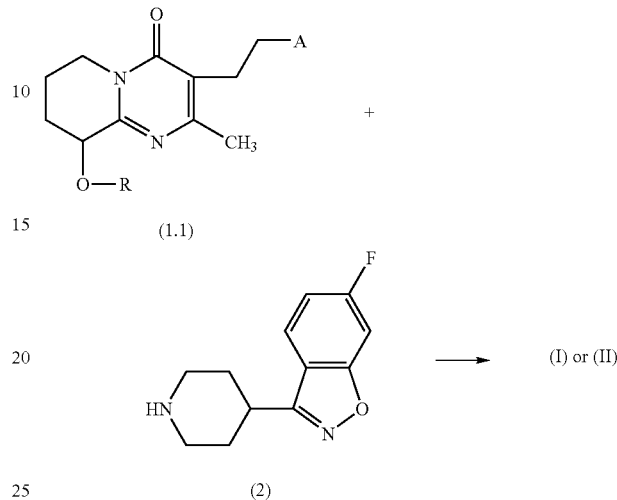

Another known process is based on the reaction of the same compound (1.1) with an oxime compound (3), wherein L is a reactive leaving group, followed by the ring closure of the isoxazole ring on the intermediate (4):

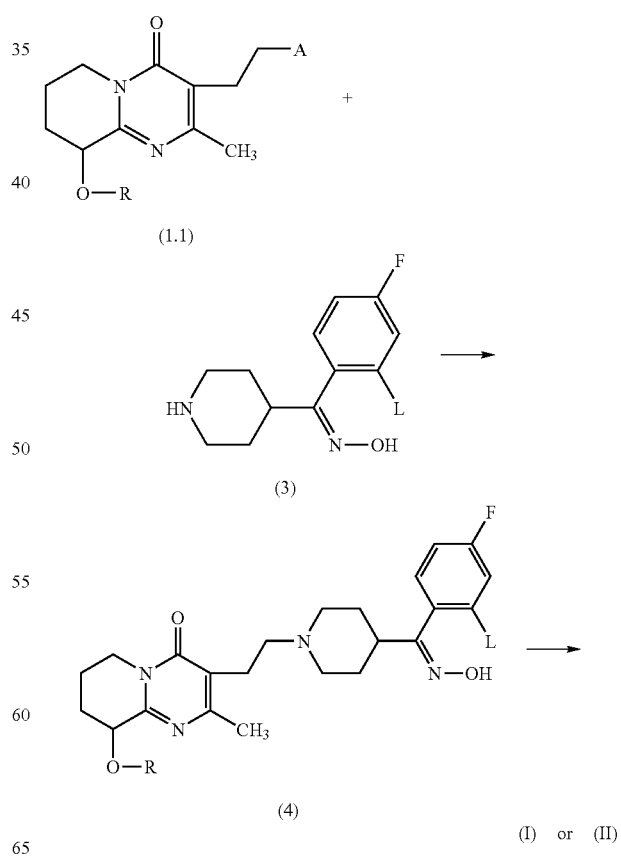

Furthermore, the esters of formula (II) may be prepared by acylating paliperidone (I) by an acylation agent (e.g. acyl halide or acyl anhydride).

As apparent, the compounds of the general formula (1.1) are valuable intermediates in making paliperidone (I) as well as the paliperidone esters of the formula (II). A typical example of the intermediate of the general formula (1.1) is the compound 3-(2-chloroethyl)-6,7,8,9-tetrahydro-9-hydroxy-2-methyl-4H-pyrido[1,2-a]pyrimidin-4-one of the formula (1a)

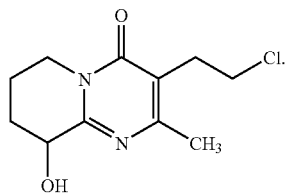

A known process for making the compounds of general formula (1.1) is based on making the corresponding O-protected starting material, followed by a reductive deprotection. An example of such process for making (1a) is shown below in Scheme I (Bn is benzyl group).

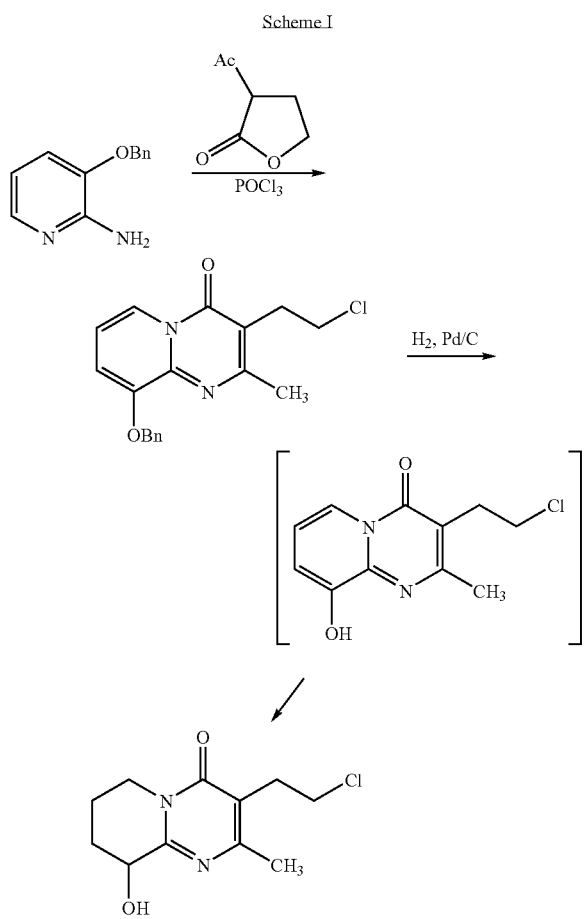

The yield in such a process is generally low, e.g. 50%, and the compound (1a) is not readily obtained as a crystalline compound under the usual reaction conditions, which is also disadvantageous.

As paliperidone is a structurally very similar to the known antipsychotic drug risperidone, the synthesis of which being very well known and elaborated, it occurred to the present inventors that it would be convenient to use risperidone or its starting materials in the synthesis of paliperidone and its O-acyl analogues. For instance, the risperidone starting materials of formula (5.1), which lacks the 9-OH group of formula (1) that is needed in the final paliperidone, are commercially available (A=Cl) and can be produced in good yields.

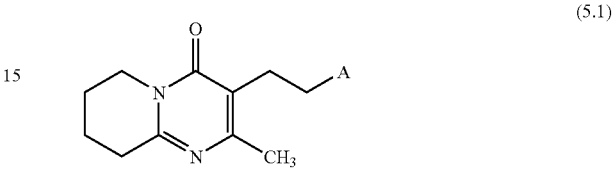

But, no process for a conversion of the compound (5.1) (or its subsequent intermediates through risperidone) into the compound (1.1) (and the corresponding subsequent intermediates through paliperidone) has been disclosed in the art. Therefore, a discovery of such a process is desirable.

SUMMARY OF THE INVENTION

The present invention relates to the discovery of a synthetic pathway for providing a 9-hydroxy or 9-ester group on risperidone or its intermediates/starting material and is thus useful in making paliperidone, its derivatives, intermediates and/or starting materials. A first aspect of the invention relates to a process, which comprises:

a) acylating under Vilsmeier-Haack or Friedel-Crafts conditions a compound of formula (5)

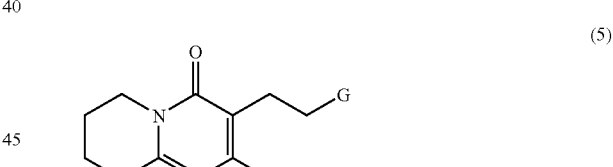

wherein G is selected from the group consisting of (i) a leaving group such as halo, e.g., chloro, bromo or iodo; or sulfonyloxy, e.g., methanesulfonyloxy, trifluoromethanesulfonyloxy, benzenesulfonyloxy, 4-methylbenzenesulfonyloxy, or 4-methoxybenzenesulfonyloxy; (ii) a group of the formula

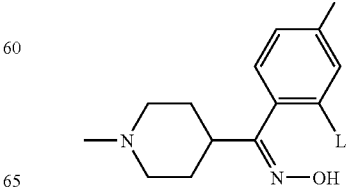

wherein L represents a reactive leaving group; and (iii) a group of the formula

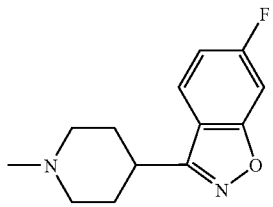

to form a compound of formula (6)

(6)

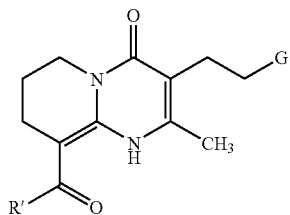

wherein R' represents hydrogen or a C1-C19 alkyl group and G is as defined above; and b) transforming said compound of formula (6) with a peroxo-compound to form a compound of formula (1)

(1)

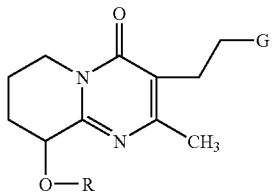

wherein R is hydrogen or C1-C20 acyl group and G is as defined above. When G represents (i) or (ii), the process can further comprise converting the compound of formula (1) into a compound of formula (10)

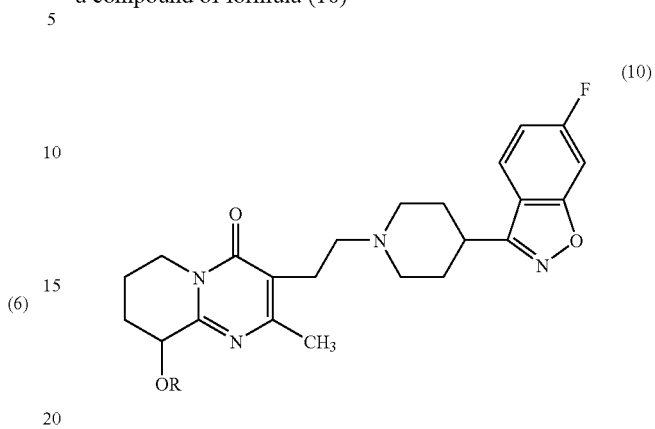

wherein R is hydrogen or a C1-C20 acyl group, and preferably R is hydrogen. When G is (iii), then the resulting compound of formula (1) is a compound of formula (10).

If R in formula (1) or (10) is hydrogen, the process may be followed with a step comprising conversion of hydrogen into C1-C20 acyl group and, conversely, if R is C1-C20 acyl group, the process may be followed with a step comprising conversion of C1-C20 acyl group into hydrogen.

DETAILED DESCRIPTION OF THE INVENTION

The present invention relates to the discovery of a two-step process for adding a 9-hydroxy/9-acyloxy group to a pyridopyrimin-4-one ring system. By use of the invention, the synthesis of risperidone can be more easily altered to produce paliperidone or the esters thereof. An overview of the possible alterations is shown below wherein the double reaction arrow represents the acylation and transformation steps of the present invention:

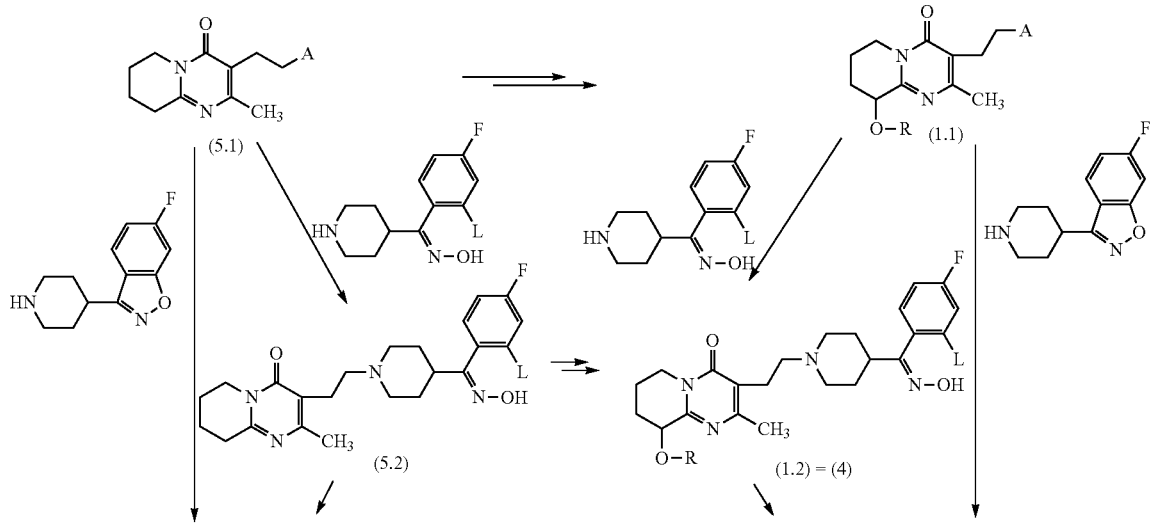

-continued

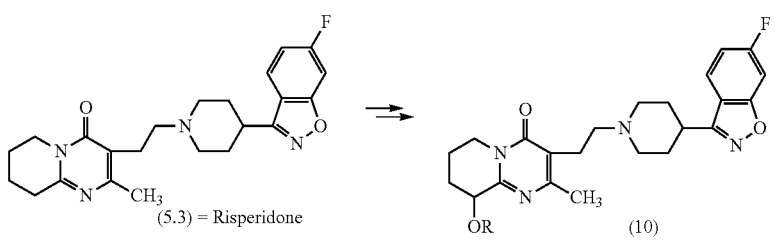
(5.3) = Risperidone

The left side reflects two conventional routes for making risperidone starting from a compound of formula (5) where G represents a leaving group "A" and denoted as compound (5.1). Subjecting a compound of (5.1) to the steps of acylation and transformation as per the present invention results in the classic paliperidone (or its ester) starting material, denoted as (1.1); e.g. a compound of formula (1) wherein G represents a leaving group "A." The two steps of the present invention can be carried out later in the risperidone process and/or on risperidone itself, e.g. using a compound of formula (5.3) as the compound of formula (5) resulting in a compound of formula (10), e.g. paliperidone or its esters.

For clarity, unless specifically stated otherwise, all formulas and compounds mentioned herein include the salts thereof, especially pharmaceutically acceptable salts, as well as the individual isomers and mixtures of isomers including racemic mixtures. Further, a "step" may include multiple reactions, conditions, and/or reagents, which can be added at one or more times, and is not limited to a single event. Thus, the "two step" process of the invention is characterized by the two general steps of acylation and transformation, as prescribed herein, and is not limited to two manipulations or specific events.

The two step process of the invention will be described and illustrated with reference to compounds of formula (5) wherein "G" represents a leaving group "A." The reaction can be represented as follows:

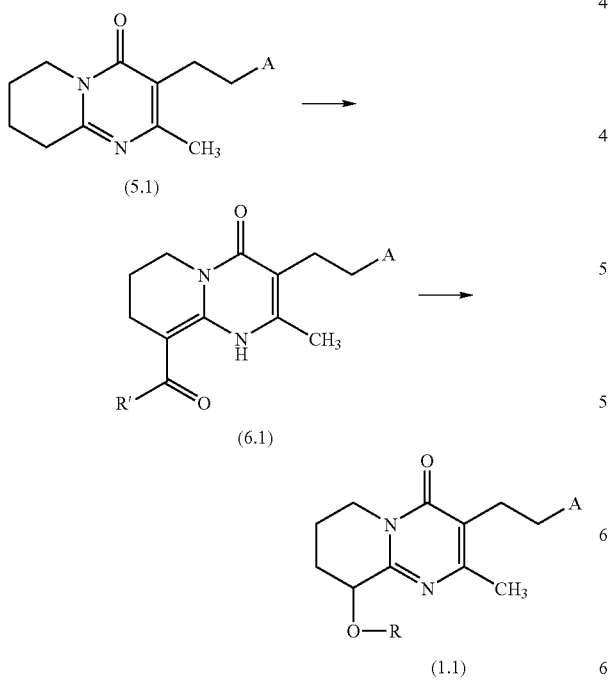

wherein R is hydrogen or C1-C20 acyl group; R' is hydrogen or a C1-C19 alkyl group; and A is a leaving group selected from halo, e.g., chloro, bromo or iodo group; and sulfonyloxy, e.g., methanesulfonyloxy, trifluoromethanesulfonyloxy, benzenesulfonyloxy, 4-methylbenzenesulfonyloxy, 4-methoxybenzenesulfonyloxy group. In a specific aspect of the above process, the compound of the general formula (5) is the compound of formula (5a),

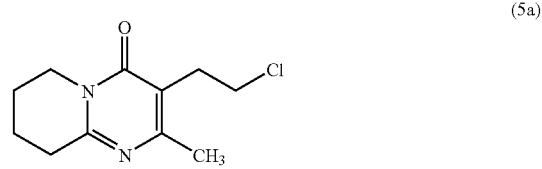

the compound of the general formula (6) is the compound of formula (6a)

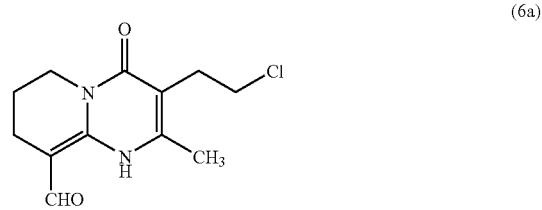

and the compound of the general formula (1) is the compound of formula (1a)

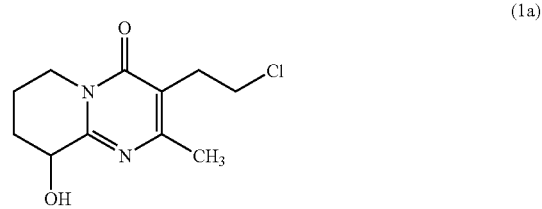

The starting material of the formula (5a) is known in the art and is commercially available. In general, it may be obtained from 2-amino pyrimidine as illustrated below in Scheme II; a process similar to Scheme I:

Scheme II.

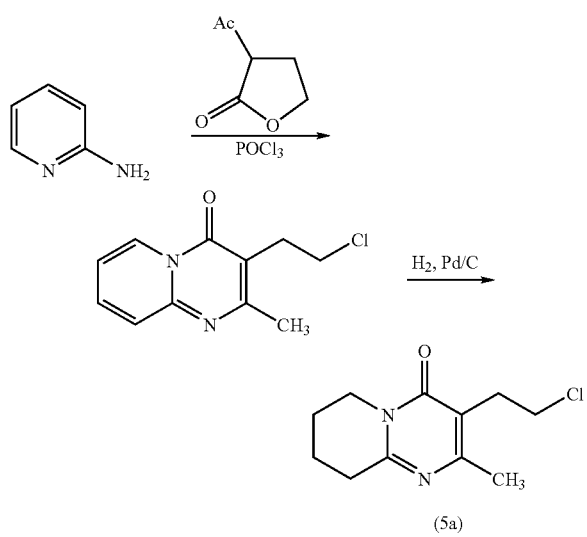

This process provides higher conversion than the process of Scheme I; i.e., Scheme I provides the compound (1a) generally with about 50% yield only. It is apparently because the presence of the 9-OH group causes the formation of side-products. Furthermore, the compound (1a) cannot be prepared in a crystalline form by the known disclosed process, contrary to the compound (5a). Thus, it can be advantageous to build up the pyrido-pyrimidine ring according to the process of the Scheme II rather than according to the process of the Scheme I, and to use the compound (5a) or more generally (5.1) in making the desired paliperidone product. The other compounds of the general formula (5.1), i.e. compounds where A is other than Cl, may be produced similarly, or may be made from the corresponding chlorine compound by the replacement of the chlorine with the alternative A-group using methods generally known in the art.

In the first step of the process of the invention, the compound of the general formula (5.1) is converted into the compound of the general formula (6.1) by an acylation of the carbon on the position 9. The acylation reaction suitably proceeds under Vilsmeier-Haack conditions or under Friedel-Crafts acylation conditions. The former is preferred for making the compounds of formula (6.1), wherein R' is hydrogen; the latter is preferred for making the compounds of formula (6.1), wherein R' is C1-C19 alkyl group.

Acylating under "Vilsmeier-Haack conditions" means that the compound (5) reacts with a Vilsmeier-Haack acylation reagent. The Vilsmeier-Haack acylation reagent is made from a tertiary amide compound (7)

R'—CO—N(R1)(R2)     (7)

wherein R' is as defined above, and an acid halide and/or donor halide compound. The compound of formula (7) is normally a formamide (e.g., R' is hydrogen) such as dialkyl formamide or aryl alkyl formamide (conveniently N,N-dimethyl formamide or N-phenyl-N-methyl formamide). The acid halide or halide donor compounds are generally phosphorous oxychloride or carbonyl dichloride, although various other compounds are known in the literature including Br$_2$/triphenylphosphine, PCl$_5$, thionylchloride, and (CF$_3$—SO$_2$)$_2$O. A review is included in WO/2007/026377. The structure of the so obtained acylation reagent (which is a methyleneiminium salt commonly known as "the Vilsmeier-Haack reagent") mostly corresponds to the formula

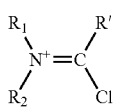

wherein R1 and R2 correspond to the alkyl or aryl substituents (the choice of which being not particularly limited and generally being a C1-C 10 alkyl or a C6-C10 aryl) on the nitrogen of the starting amide compound (7) and R' is hydrogen or C1-C19 alkyl group, preferably hydrogen). For N,N-dimethylformamide, which is the typical amide compound (7) for the Vilsmeier-Haack reaction, the R' is hydrogen, and R1, R2 are methyl groups. The formula covers most of the Vilsmeier-Haack reagents, but not all, depending on the acid halide/donor halide compound used. For example, when the carbonyl dichloride (phosgene) is used, then the Cl in the formula is replaced by a —OCOCl group. Similarly, if bromine/triphenylphosphine is used, then the Cl is replaced by Br, etc.

The acylation reaction under conditions of Vilsmeier-Haack reaction is particularly suitable for making compounds of formula (6.1), wherein R' is hydrogen. In particular, the compound of formula (5a) and the Vilsmeier-Haack reagent made from N,N-dimethylformamide and phosphorous oxychloride, provides exclusively the compound (6a). The reaction runs under mild conditions, with a high yield, providing a product with high purity.

The Vilsmeier-Haack reaction is normally used with activated aromatic compounds such as anilines or phenols. Horvath et al. (J. Chem. Soc. Perkin Trans. 1, (1983) p. 369) studied this reaction on the pyrido-pyrimidine system and found that the reaction provides a product substituted on the position 9; but, dependent on the nature of other substituents in the pyrido-pyrimidine system, the substituent was an aldehyde or a dimethylaminomethylene, as well as a mixture of both products. In contrast, the present inventors found that the starting material of the formula (5a) provides preferentially the acylated product of the formula (6a) under the conditions of the Vilsmeier-Haack reaction, particularly by the Vilsmeier-Haack reagent made from N,N-dimethylformamide and phosphorous oxychloride.

In accordance with the general knowledge about the mechanism of Vilsmeier-Haack reaction, the primary product of the acylation reaction of the compound (5a) is likely the compound of the formula (8a)

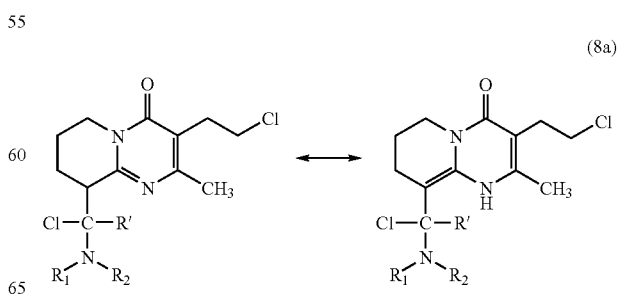

and a secondary product (after an elimination of HCl from the (8a)) is the dialkylaminomethylene product (8b)

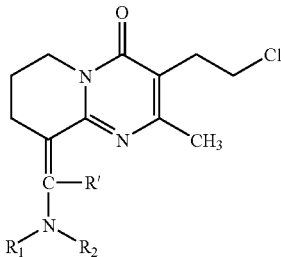
(8b)

Both compounds (8a) and (8b) are hydrolysed during the elaboration of the reaction mixture to the final product, the compound (6a). The subsequent hydrolysis, which is generally carried out by the addition of water and preferably under alkaline conditions, is considered part of the Vilsmeier-Haack conditions for acylation.

The acylation reaction is generally performed in a solvent. The solvent can be inert, such as an aliphatic or aromatic hydrocarbon or a chlorinated hydrocarbon. Alternatively, the amide reagent can conveniently serve also as the solvent or co-solvent for the reaction. In such a case, it is possible, but not required, to prepare the Vilsmeier-Haack acylation reagent prior to the addition of the substrate, i.e. to mix the amide reagent and the halogen reagent prior to adding the compound (5.1) into the system.

The reaction temperature is not particularly limited and is conveniently from around 0° to 100° Celsius (e.g. +/−5°), advantageously with a gradual increase of the temperature. The reaction time is usually 2 to 4 hours, but can be longer.

The reaction mixture is conveniently elaborated by a hydrolysis with water, suitably together with a neutralization of the aqueous reaction mixture with a base, advantageously with an alkaline carbonate such as sodium hydrogen carbonate.

The reaction product of the formula (6.1) may be isolated from the neutralised reaction mixture by conventional means, such as by filtration or by an extraction into an organic solvent and isolation from the solvent by evaporation of the solvent or precipitation from the solvent, and further purified, if necessary. For instance, the preferred compound of the formula (6a) may this way be isolated in the solid state and may be further crystallized from a convenient solvent, e.g., from ethyl acetate.

The process may yield the compound (6.1), and particularly the compound (6a), in a chemical purity higher than 95% and even higher than 99%, which is very useful in respect to the purity of the product in the next step of the process of the present invention.

Alternatively, the acylation can be carried out under "Friedel-Crafts conditions" of acylating; meaning that the compound of formula (5.1) reacts with an acylation agent, which is C1-C20 acylhalide or acylanhydride, typically acylchloride, under presence of a Lewis acid which generates the corresponding acyl cation. The Lewis acid is typically an acidic metal halide such as aluminium trichloride. It was found by the present inventors that the reaction proceeds selectively on the position 9 of the compound (5.1), i.e. the other hydrogens of the pyrido-pyrimidinone ring are not attacked.

The acylation reaction under conditions of Friedel-Crafts reaction is particularly suitable for making compounds of formula (6.1), wherein R' is C1-C19 alkyl group.

The reaction is performed in a solvent, such as an aliphatic hydrocarbon or chlorinated hydrocarbon, or the acylation agent serves as the solvent. At least one molar equivalent of the Lewis acid, particularly aluminium trichloride is generally required. The reaction temperature is generally higher than ambient, from 30 degrees Celsius to the reflux temperature. After the reaction is completed, the reaction mixture is treated by water to decompose the aluminium chloride, and the product of formula (6.1) is isolated, suitably after neutralization, from the organic phase by evaporation of the solvent or precipitation from the solvent.

In the second step, the compound of formula (6.1) is transformed into a compound of formula (1.1) by the use of a peroxo-compound. A "peroxo-compound" includes hydrogen peroxide, preferably in a combination with an acid (preferably organic acid and most preferably formic acid), a peracid (e.g. peracetic, pertrifluoroacetic, m-chloroperbenzoic acid or perbenzoic acid etc.), or an organic peroxide. The peroxo-compound is able to react with the compound (6.1) by a mechanism that is similar to a Baeyer-Villiger rearrangement reaction. Simply said, the peroxo-compound "splits" the bond between the carbons of the carbonyl group and of the pyrimidine ring and "inserts" an oxygen linkage between both of these parts of the molecule. Accordingly, the primary product of the reaction of the peroxo-compound with the compound (6a) is an alkanoate of the formula (9a) [R' is hydrogen or C1-C19 alkyl group],

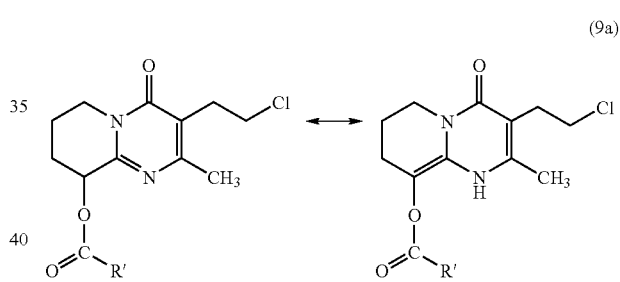
(9a)

which formula represents a subgroup of compounds corresponding to the formula (1) and formula (1.1), in which A=Cl and R is C1-C20 acyl group, i.e. not hydrogen. The compound (9a) may be isolated from the reaction mixture and represents the desired product within the general formula (1.1). The preferred desired compound of the formula (9a) contains R' as a C15H31 linear alkyl group and is represented by the following formula (1b):

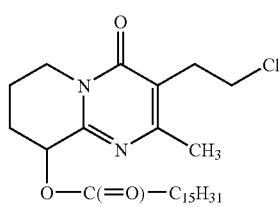
(1b)

Alternatively, the formed ester compound (9a) may be hydrolysed (preferentially by an alkaline hydrolysis) to the alcohol of formula (1a), either in situ (in the reaction mixture) or in a separate technological step after the isolation of the compound (9a).

Reaction of (6a) with a peroxo-compound under acidic or alkaline conditions may provide the compound (1a) directly, as the compound (9a) is often not stable under these conditions and hydrolyses the acyl group in situ. If other than compound (1a) is desired, it may also be made by esterification of the formed (1a) with a reactive derivative (acyl halide or acyl anhydride) of the corresponding C1-C19 acid, by conventional means. Thus either hydrolysis to form R as hydrogen or esterification to form R as C1-C20 acyl group are included within the transforming step.

The process of the second step typically proceeds in a solvent, which may be an aqueous or non-aqueous solvent inert to the peroxo-compound. From the peroxo-compounds listed above, the useful agent is typically the aqueous hydrogen peroxide in combination with formic acid, or an organic peracid. Convenient reaction temperature is from 40 degrees Celsius to a reflux temperature, wherein the reaction time is 1-3 hours.

Reaction mixture may be elaborated to remove the rest of the reagents and neutralized, if necessary, and the desired product isolated, preferably in solid state, by removal of the solvent or by a precipitation from a solution. Yield of the reaction is generally about 60-70%, purity of the crude product is generally higher than 85%.

The crude product of formula (1a) may then be optionally recrystallised from a convenient solvent, for instance from an ether solvent, and a product of the purity higher than 95% may be easily obtained.

The finding that it is possible to use the reaction conditions of the Baeyer-Villiger reaction for the conversion of the 9-acyl group into the 9-hydroxy/acyloxy group on the pyridopyrimidinone ring is a surprise as the Baeyer-Villiger reaction is normally used for aromatic compounds, preferably for those that are activated by a suitable substituent in o- or p-position.

In summary, the above process of the present invention starts from cheap starting materials, does not require using protective groups, runs under mild reaction conditions and proceeds with excellent yields and purity of the product. Accordingly, the whole process for making paliperidone and esters thereof can be more economical.

The product of general formula (1.1) may then serve as a starting material for the synthesis of paliperidone as well as derivatives thereof, including pharmaceutically acceptable salts and the stereochemically isomeric forms thereof. The conversion of the compounds of formula (1.1) into paliperidone or its esters is generally well known as shown above. The compound of formula (1.1) can be alkylated with a compound of formula (2) and directly form a compound of formula (10):

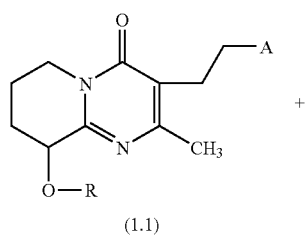

(1.1)

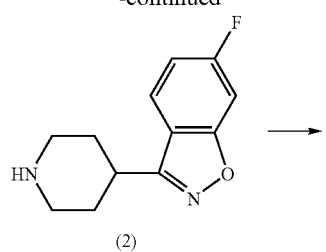

(2)

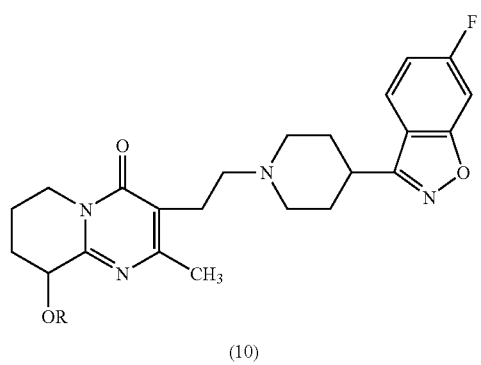

(10)

When R in formula (10) is hydrogen, the compound is paliperidone. Likewise the conversion of (1.1) to (10) can comprise alkylating with a compound of formula (3) to form a compound of formula (4) followed by ring closure, as described above. The conditions of the conversion reactions are well known in the art. Additionally, the compound (1.1) may serve as starting material for the synthesis of the 9-tetrahydropyranyl paliperidone derivative disclosed in U.S. provisional patent application Ser. No. 60/952,376, filed Jul. 27, 2007. Similarly, compounds of formula (1.1) can be used for making esters of paliperidone, e.g., paliperidone palmitate may be advantageously made from the compound (1b). The possibility to obtain the starting compound in a high purity allows for making such paliperidone compounds with higher yields and with less burden in purification to achieve pharmaceutically acceptable quality.

While the use of a compound of formula (5.1) as a starting material and resulting compound of formula (1.1) is contemplated as the most likely use of the present invention, it is not limited thereto. The group G in formula (5) can be other than a leaving group, yet the above sequence of the reaction steps may be, mutatis mutandis, used for a conversion of compounds of the formula (5) to a compound of formula (1). For example, when G represents an oxime, the compound of formula (5) can be expressed as formula (5.2) (L is advantageously the fluoro-group). Under the conditions described above, the compound (5.2) can be acylated under Vilsmeier-Haack or Friedel-Crafts conditions to form a compound of formula (6.2), which in turn is transformed into a compound of formula (1.2), a well known paliperidone intermediate compound.

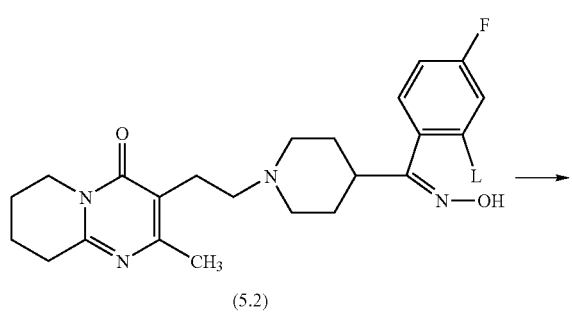

(5.2)

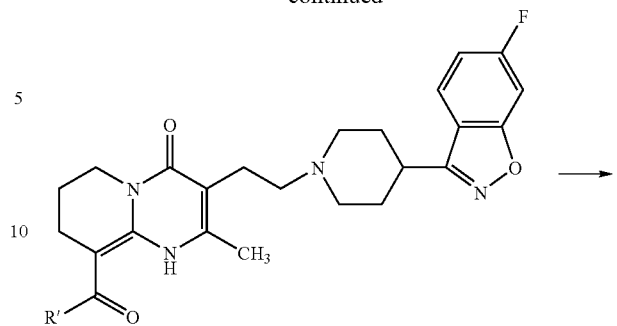

(6.3)

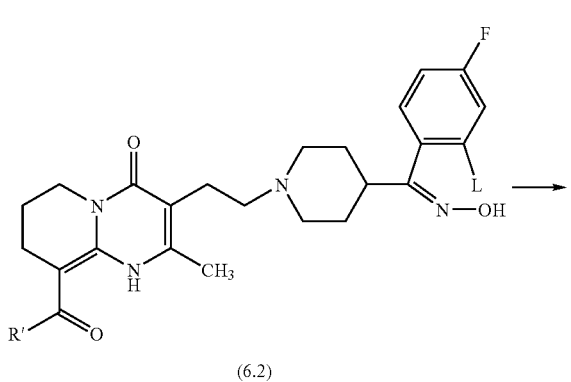

(6.2)

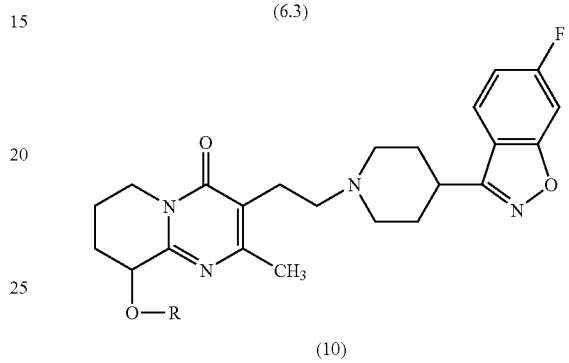

(10)
(I) R = H
(II) R = C1-C20 acyl

As mentioned above, conversion between the hydrogen or C1-C20 acyl group of R in all of the compounds of formula (1), e.g. (1.1), (1.2), and (10), is possible as part of the transforming step and/or as a separate step. The conversion from one group to the other can be carried out by methods and techniques known in the art and can afford further flexibility in the synthesis.

The invention is illustrated by the following examples.

EXAMPLES

Example 1

Compound (6a)

Into 390 ml of N,N-dimethylformamide, 50 ml of POCl$_3$ was added dropwise in 25 minutes, wherein the internal temperature was maintained at a temperature between −2 and 0° C. The mixture was stirred at a temperature between −1 and 0° C. for 80 min. Then a solution of 111.8 g of Compound (5a) in 150 ml of N,N-dimethylformamide was added dropwise at a temperature between −1 and +1° C. in 35 min. Then the reaction mixture was stirred at temperature 0° C. for 30 min and the temperature was gradually increased to 25° C. in 40 min. The reaction mixture was then warmed to 80° C. The reaction progress was monitored by HPLC.

After 90 min, the reaction mixture was cooled down to 20° C. and poured onto 800 g of crushed ice. The mixture was stirred and neutralized with Na$_2$CO$_3$ (70 g) to pH 7-7.5. During the neutralization, a precipitate was formed.

The heterogenic mixture was stirred with 500 ml of dichloromethane. The layers were separated and aqueous layer washed with 5×200 ml of ethyl acetate. The combined organic layers were washed with 7×200 ml of water, dried by anhydrous sodium sulphate and filtered with charcoal over celite.

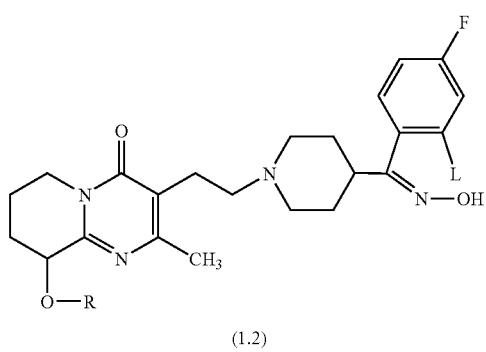

(1.2)

Similarly, when G in formula (5) represents 4-(6-fluoro-1,2-benzisoxazol-3-yl)-1-piperidinyl group, the compound can be expressed as formula (5.3), which is also known as risperidone. Nonetheless, the two steps of acylation and transformation outlined above can be applied, mutatis mutandis, under similar reaction conditions, to convert risperidone (5.3) into a paliperidone compound (10) as shown below.

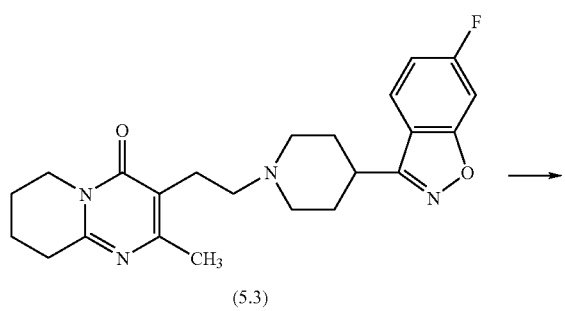

(5.3)

The solvent was evaporated (50° C.), yielding 115.5 g (91.8%) of a solid. HPLC purity: 97.52% (IN)

Purification:

115.5 g of raw compound (6a) from the preceded step was dissolved in 300 ml of dichloromethane. The solution was filtered over 50 g of silica gel layer (10 cm). The silica gel was washed with 200 ml of dichloromethane. The combined filtrate was mixed with 150 ml of ethyl acetate at 50° C. The dichloromethane was evaporated and ethyl acetate solution cooled down to temperature 5° C. The formations of fine crystals were observed. The heterogenic mixture was stirred for 1 h at 5° C. and the solid filtered by suction. The filtration cake was washed with 2×50 ml of cold ethyl acetate (0° C.) and dried at room temperature.

Yield: 87 g (75%) of off white fine crystalline material. HPLC: 99.86% (IN)

Example 2

Compound (1a)

4.0 g of aldehyde (6a) was stirred with 80 ml of dichloromethane. The mixture was cleared immediately.

4.0 ml of 30% aqueous hydrogen peroxide and 2.4 ml of formic acid were added to the solution. The mixture was warmed to reflux. After 60 minutes, the reaction mixture was cooled down to room temperature and neutralized solid NaHCO$_3$ to pH 7-8. The layers were separated, the organic layer washed with 3×15 ml of brine and with 2×15 ml of water, dried by anhydrous sodium sulphate and filtered with activated charcoal via Celite. The solvent was evaporated (50° C., 560-10 mbar).

Yield: 3.3 g (86.6%) of slight yellow solid. Purity of product: 84% (HPLC, IN)

Purification:

3.3 g of raw (1a) was stirred with 20 ml of diethyleter at reflux. The mixture was cooled down and stirred for 1 h at 0-4° C. The precipitate was filtered by suction and the solid material washed 2×5 ml of cold diethyleter (0° C.).

Yield: 1.5 g (56% calculated on raw (1a)) of off white solid material. Purity of product: 96% (HPLC, IN).

Example 3

Compound (1a)

50 g of the aldehyde (6a) was stirred with 100 ml of dichloromethane at 30° C. The solid material was completely dissolved. Then solid m-chloroperbenzoic acid (42.34 g) was added in parts during 240 minutes. The internal temperature of reaction mixture was kept at 30° C. The reaction mixture was analyzed by HPLC.

The reaction mixture was stirred with 100 ml of water and neutralized with 46 g of solid NaHCO$_3$ (, pH 7-8) within 90 min. The reaction mixture was cooled (to 11° C.) and allowed to stand for separation of layers. The layers were separated and organic layer washed with 5×100 ml of water, dried by solid sodium sulphate and filtered with activated charcoal over celite. The solvent was evaporated and 25 ml of methyl tert.butyl ether was added to the residue. The mixture was stored at 5° C. for 17 h. The solid material was filtered by suction and washed with 2×15 ml of cold methyl tert.butyl ether.

Yield: 18.5 g (38.8%) of slight yellow solid. Purity: 89% (HPLC, IN)

Each of the patents, patent applications, and journal articles mentioned above are incorporated herein by reference in their entirety. The invention having been thus described it will be obvious that the same may be varied in many ways and all such modifications are contemplated as being within the scope of the invention as defined by the following claims.

We claim:

1. A process, which comprises:

a) acylating under Vilsmeier-Haack or Friedel-Crafts conditions a compound of formula (5)

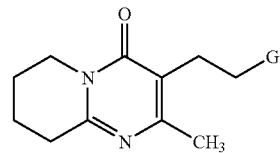

(5)

wherein G is selected from the group consisting of (i) a leaving group; (ii) a group of the formula

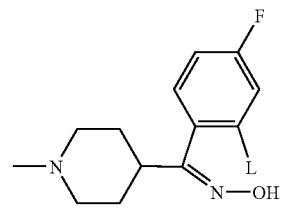

wherein L represents a reactive leaving group; and (iii) a group of the formula

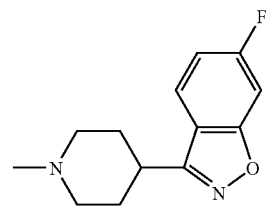

to form a compound of formula (6)

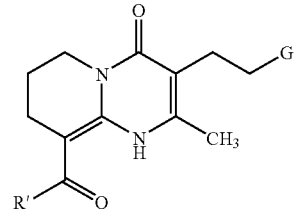

(6)

wherein R' represents hydrogen or a C1-C19 alkyl group and G is as defined above; and b) transforming said compound of formula (6) with a peroxo-compound to form a compound of formula (1)

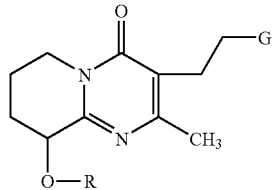

(1)

wherein R is hydrogen or C1-C20 acyl group and G is as defined above.

2. The process according to claim 1, wherein G represents a leaving group selected from the group consisting of chloro, bromo or iodo, methanesulfonyloxy, trifluoromethanesulfonyloxy, benzenesulfonyloxy, 4-methylbenzenesulfonyloxy, and 4-methoxybenzenesulfonyloxy.

3. The process according to claim 1, wherein G represents chloro.

4. The process according claim 1, wherein said acylation is carried out under Vilsmeier-Haack conditions and R' and R are hydrogen.

5. The process according to claim 4, wherein said Vilsmeier-Haack conditions include combining a N,N-dimethyl formamide with a phosphorous oxychloride to form a Vilsmeier-Haack reagent.

6. The process according to claim 5, wherein said compound of formula (5) is a compound of formula (5a), said compound of formula (6) is a compound of formula (6a) and said compound of formula (1) is a compound of formula (1a):

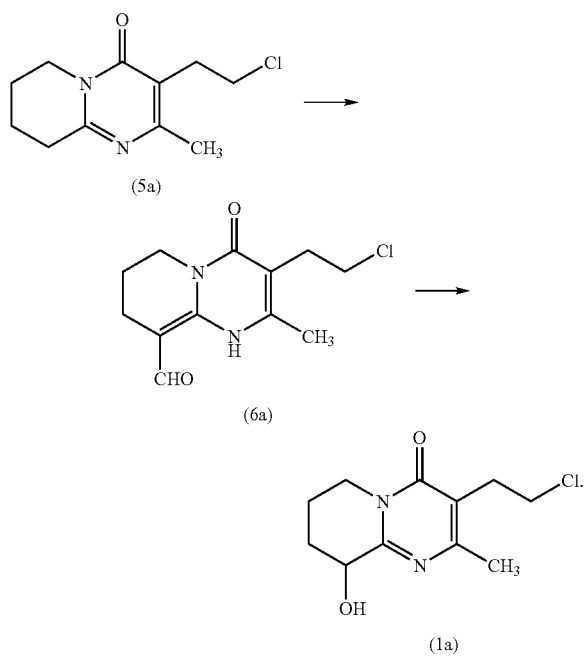

7. The process according to claim 1, wherein said peroxo-compound is hydrogen peroxide, optionally further in combination with formic acid.

8. The process according to claim 1, which further comprises converting said compound of formula (1) into a compound of formula (10)

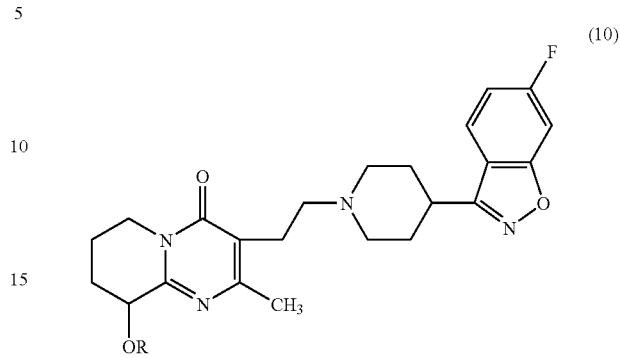

(10)

wherein R is hydrogen or a C1-C20 acyl group.

9. The process according to claim 8, wherein said conversion comprises reacting said compound of formula (1), wherein G represents a leaving group, with a compound of formula (2)

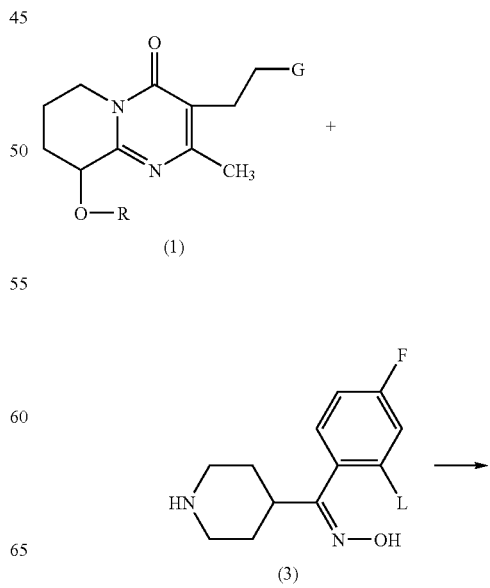

to form said compound of formula (10).

10. The process according to claim 8, wherein said conversion comprises:

reacting said compound of formula (1), wherein G represents a leaving group, with a compound of formula (3) to form a compound of formula (4)

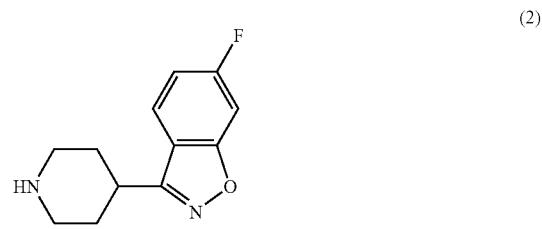

-continued

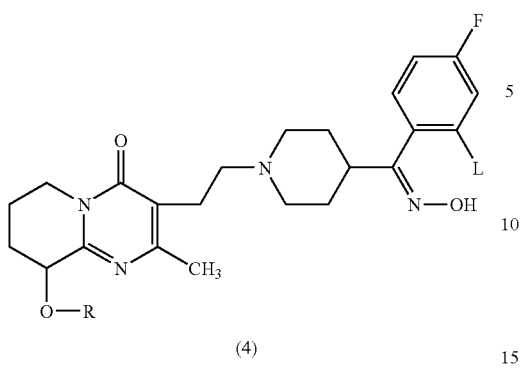

wherein L represents a reacting leaving group; and
subjecting said compound of formula (4) to ring closure to form said compound of formula (10).

11. The process according to claim 8, wherein R and R' in formulas (5), (6), and (1) represent a hydrogen, and said conversion forms a compound of formula (10) wherein R is hydrogen.

12. The process according to claim 1, wherein R' is a C1-C19 alkyl group and said acylating step is carried out under Friedel-Crafts conditions.

13. The process according to claim 12, wherein R' is a C15 alkyl group.

14. The process according to claim 12, wherein R in formula (1) is hydrogen.

15. The process according to claim 12, which further comprises converting said compound of formula (1) into a compound of formula (10)

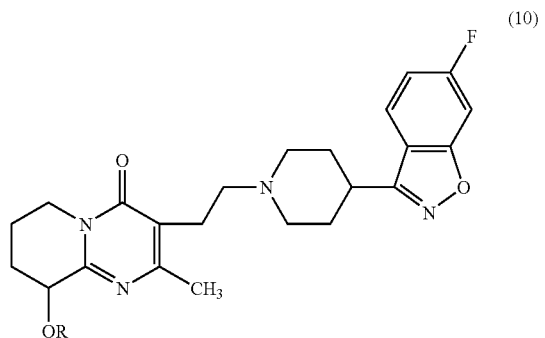

wherein R is hydrogen or a C1-C20 acyl group.

16. The process according to claim 1, wherein G represents a group of the formula

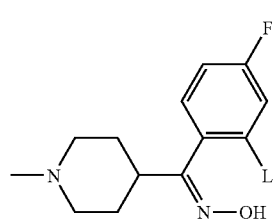

and said compound of formula (1) is compound of formula (1.2)

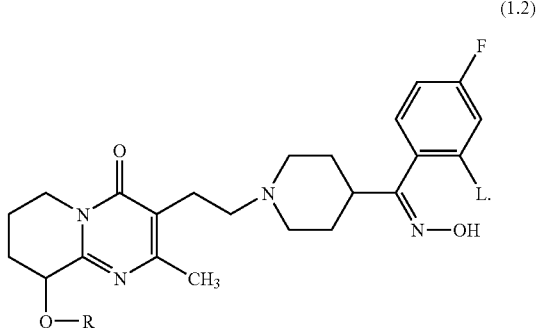

17. The process according to claim 15, which further comprises subjecting said compound of formula (1.2) to ring closure to form a compound of formula (10)

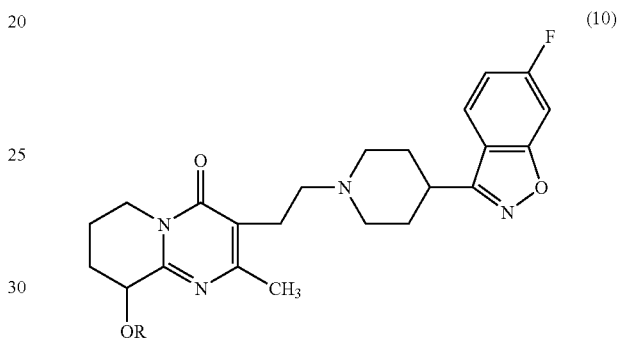

wherein R is hydrogen or a C1-C20 acyl group.

18. The process according to claim 1, wherein G represents a group of the formula

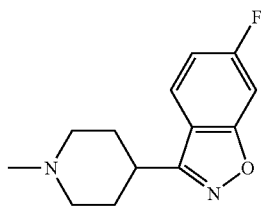

and said compound of formula (1) is a compound of formula (10)

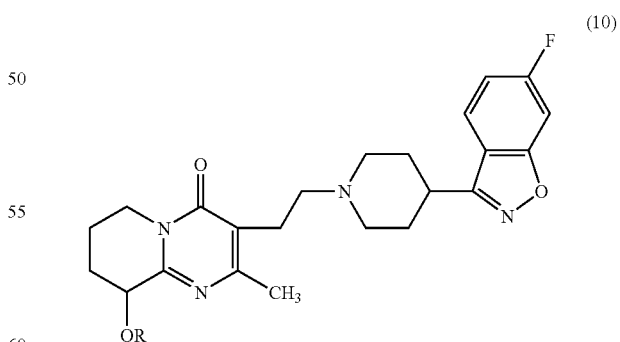

wherein R is hydrogen or a C1-C20 acyl group.

19. The process according to claim 1, which further comprises, when R in formula (1) represents hydrogen, converting R into a C1-C20 acyl group; and when R in formula (1) represents a C1-C20 acyl group, converting R into hydrogen.

* * * * *